United States Patent [19]
Pond et al.

[11] Patent Number: 5,876,381
[45] Date of Patent: Mar. 2, 1999

[54] ANTI-STICK ADAPTOR FOR HYPODERMIC DENTAL NEEDLES

[75] Inventors: Gary J. Pond, Racine, Wis.; Michael S. Butler, Round Lake Heights, Ill.

[73] Assignee: Inter-Med, LLC., Racine, Wis.

[21] Appl. No.: 8,517

[22] Filed: Jan. 15, 1998

[51] Int. Cl.⁶ .................................................. A61M 5/32
[52] U.S. Cl. ......................... 604/192; 128/919; 206/365; 206/368
[58] Field of Search .................................. 604/263, 192, 604/110; 206/363, 364, 365, 366, 367, 368, 369, 370; 128/917, 919

[56] References Cited

U.S. PATENT DOCUMENTS

| 4,982,842 | 1/1991 | Hollister . |
| 5,417,926 | 5/1995 | Bouveret ................................. 206/364 |

*Primary Examiner*—Ronald Stright, Jr.
*Attorney, Agent, or Firm*—Ryan Kromholz & Manion, S.C.

[57] ABSTRACT

A safety adapter for hypodermic needles and, in particular, double-ended needles of the type used in dental procedures. The adapter comprises two sections coupled together as a unitary device. One section is arranged to receive and house one of the projecting needles and the other section houses and protects the oppositely directed needle.

5 Claims, 3 Drawing Sheets

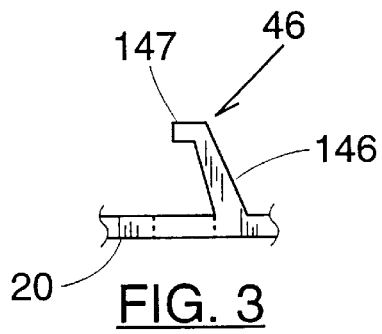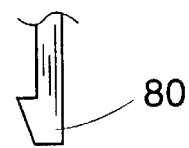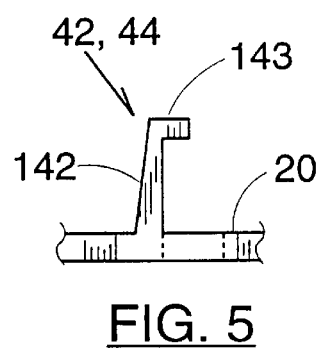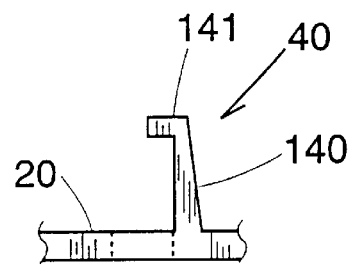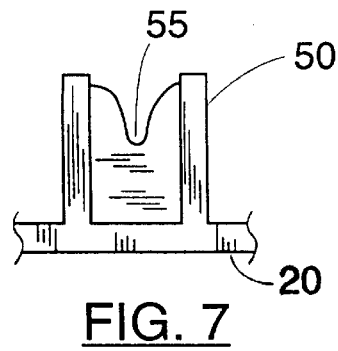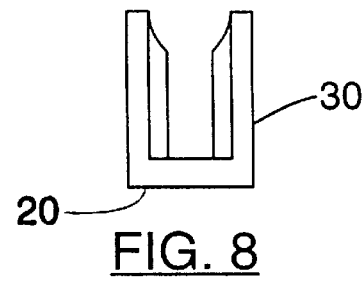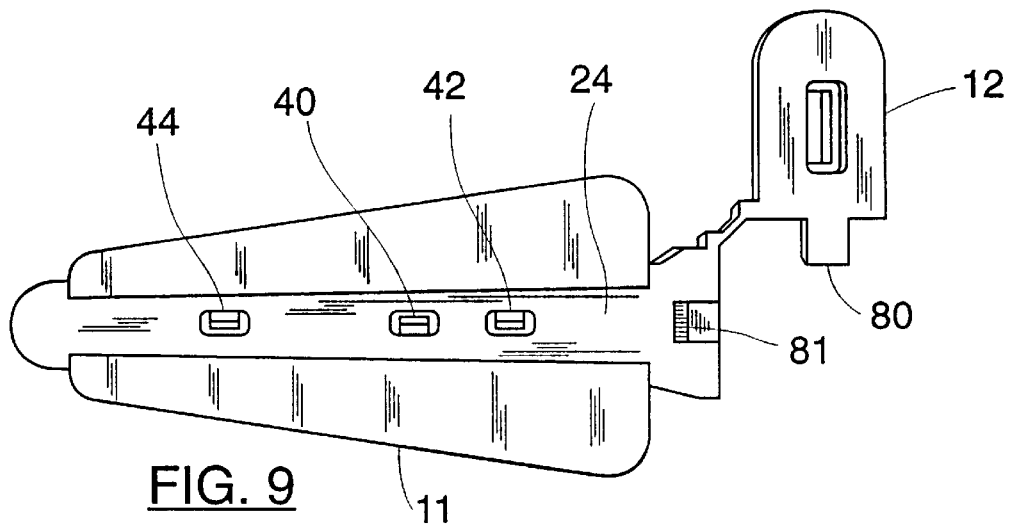

ANTI-STICK ADAPTOR FOR HYPODERMIC DENTAL NEEDLES

BACKGROUND OF THE INVENTION

The present invention relates generally to a safety adapter for hypodermic needles, and specifically to an anti-stick adapter for hypodermic needles. The device is capable of housing a hypodermic needle of the type used in dental procedures, such that a person handling the needle will not be accidentally stuck by it.

The present invention addresses the concern for an improved and safe handling of a hypodermic needle. We live in an era of increased awareness to infectious diseases. In handling sharp medical instruments, such as hypodermic needles, there is always a chance that the user, or persons situated in the proximity of the medical instruments, may be exposed to cuts or stings. Therefore, an urgent need exists for safety measures and adapters designed to prevent accidental injury and infection due to contaminated medical instruments.

Several inventions and designs have addressed the issue of a safety adapter for guarding a needle. It has long been known in the prior art to provide pivotable safety adapters connected to the syringe and guarding the needle. However, these adapters appear to involve mating with the ejection end of the syringe and do not solve the additional problems created by a hypodermic needle used in surgical dental procedures. In this regard, the hypodermic syringe assembly frequently used by dentists comprises a luer and two needles, located on each side of the luer, opposite to one another. The first needle is longer and its end passes through the patient's tissue to deliver medication. The second needle is shorter and its end pierces a canister located within a syringe which contains the medication. The luer is used to attach the two needles to the syringe.

As an example of the prior art, U.S. Pat. No. 4,982,842 to Hollister teaches a safety adapter having two sections and a housing flexibly connected to one of the sections. The first section is adaptable to be mated with the hub of a needle assembly, while the second section is adaptable to different types of syringes. The pivotable housing surrounds the needle and a retainer mechanism in the housing prevents movement between the needle and the housing. However, when the needle assembly is removed for disposal, there is no readily available protection for the second needle hidden inside the syringe. Therefore, there still remains a need for an anti-stick adapter that is adaptable to be used with different types of needles, including needles used by dentists.

It is an object of this invention to provide an anti-stick adapter adaptable to hypodermic needles used by dentists in dental procedures. It is another object of the present invention to provide such an adapter that is safe and easy to use.

SUMMARY OF THE INVENTION

The present invention relates generally to safety adapters for hypodermic needles and, more particularly, to an anti-stick adapter for containing hypodermic needles used in dental procedures.

The anti-stick adapter is preferably molded as a unitary structure with a first and a second section integrally hinged for movement with respect to one another. The first section includes a base and a housing supported by the base and defining enclosure walls with an opening at the hinge end of the first section. The housing of the first section preferably contains three longitudinally spaced locking members integrally molded to the base of the first section and each including a hook-like portion arranged for securely retaining a first needle within the protective housing. The intermediate locking member preferably has its hook-like portion facing in a direction opposite to the hook like portions of the longitudinally spaced locking members. A pair of integrally molded, upstanding support, web-like members are disposed between the intermediate locking member and its spaced outer locking member. Each of these support members is preferably formed to define a V-shaped notch at its outer end to form a channel for securely supporting and retaining the first needle within the first section housing.

The integrally molded second section of the anti-stick adapter also preferably includes a single locking member having a hook-like portion facing in the same direction as the intermediate hook-like portion of the intermediate locking member (compare FIGS. 3 and 6). As stated above, the first and the second sections of the device are preferably secured together by means of an integrally formed hinge section. A locking mechanism is also provided to hold the first and second sections together for retention of a double-ended hypodermic syringe having oppositely disposed needles.

After the dentist uses a hypodermic needle attached to a syringe to administer medication to a patient, he or she will insert the syringe with the first needle into the first housing, such that the first needle engages with the first section locking members and with the aid of the two support members positioned between the longitudinally spaced locking members. Next, the dentist can disengage the luer from the syringe, thereby exposing the second needle. Finally, the second section is pivoted about its hinge, thereby wrapping around and covering the second needle and securely retaining it within the second section housing. The locking mechanism of the second section will snap into place due to the inherent flexibility of the preferred molding. Thereby the section will be coupled together in order to safeguard the two needles and substantially eliminate the possibility of deleterious "sticking" of the dentist or the patient or anyone assisting the dentist.

DESCRIPTION OF THE DRAWINGS

FIG. 3 is a cross-sectional view of the second section locking member, taken along line 3—3 of FIG. 2.

FIG. 4 is a cross-sectional view of the locking member, taken along line 4—4 of FIG. 2.

FIG. 5 is a cross-sectional view representing each substantially identical locking members of the first section of the device, taken along lines 5—5 of FIG. 2.

FIG. 6 is a cross-sectional view of the intermediate first section locking member, taken along line 6—6 of FIG. 2.

FIG. 7 is a cross-sectional view representing each of the first section support members, taken along each of lines 7—7 of FIG. 2.

FIG. 8 is a cross-sectional view of the housing of the first section of the adapter, taken along line 8—8 of FIG. 2.

FIG. 9 is a bottom plan view of the present invention.

DETAILED DESCRIPTION

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

Figure 1:
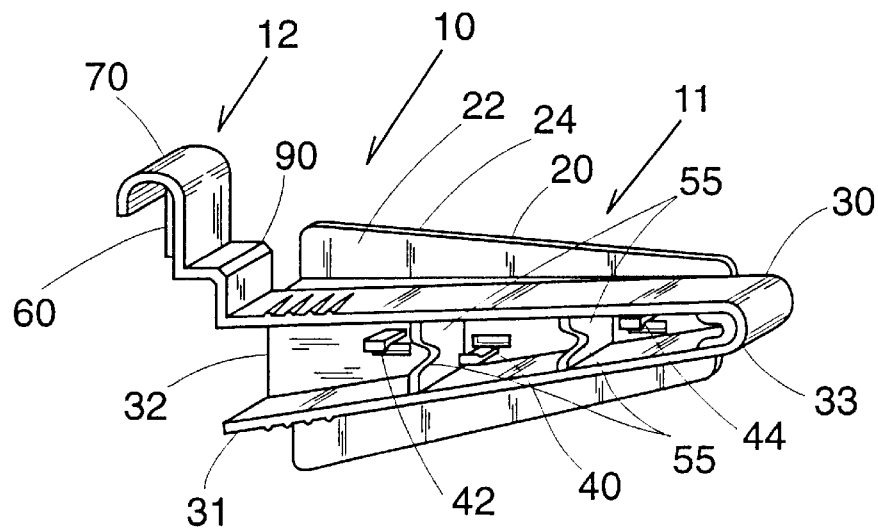
FIG. 1 is a perspective view of the present invention, showing the anti-stick adapter.

The preferred embodiment of the anti-stick adapter is designated generally by the reference numeral 10 as illustrated in FIG. 1.

Figure 2:
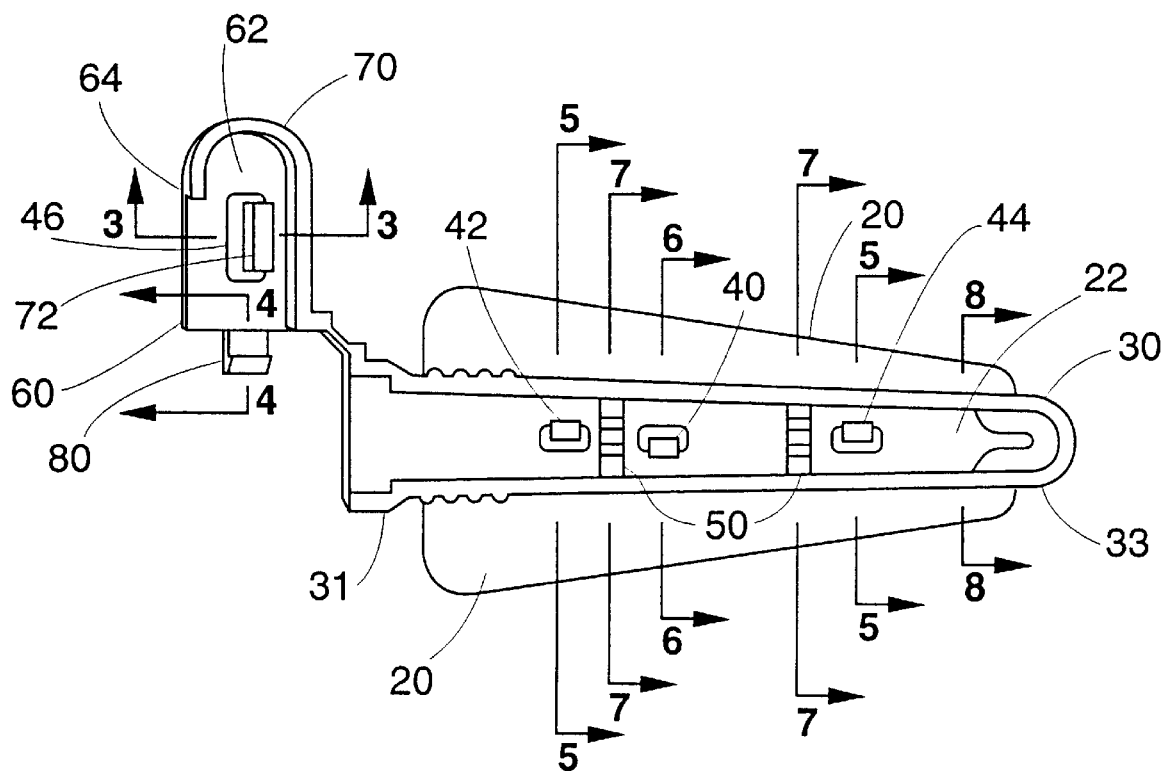
FIG. 2 is a top plan view of the anti-stick adapter of FIG. 1.
Figure 10:
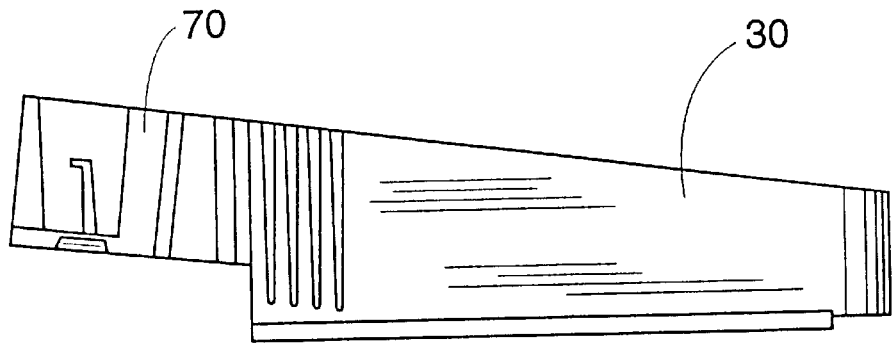
FIG. 10 is a side view of the present invention.
Figure 11:
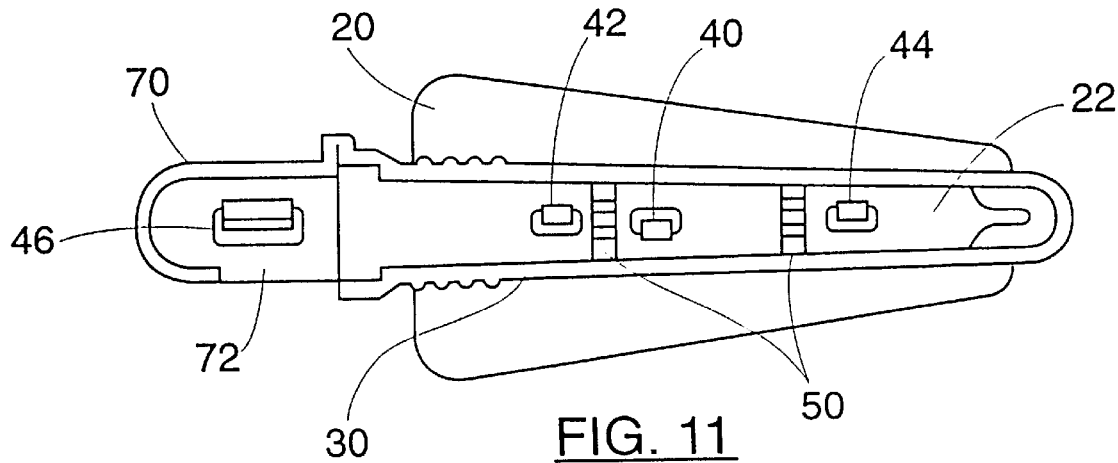
FIG. 11 is a top plan view showing the second section pivoted about its hinge to locking position in substantially coplanar relationship with the first section.
Figure 12:
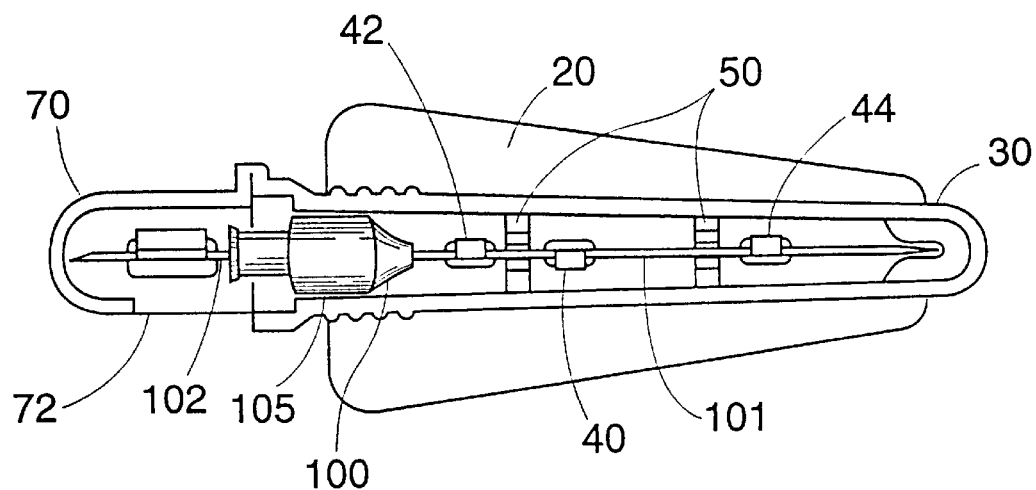
FIG. 12 is a top plan view, showing the second section pivoted about its hinge and in locking engagement with the first section, and further illustrating a hypodermic needle assembly within the present invention.

With particular reference to FIGS. 1 and 2, the anti-stick adapter 10 is preferably molded by well-known injection molding techniques to provide integrally coupled first section 11 and second section 12, integrally joined together by a hinge section 90, and arranged for locking closure with respect to one another by means of a locking mechanism 80. The first section 11 comprises a first base 20 having a top surface 22 and a bottom surface 24. The bottom surface 24 is preferably flat and integrally molded with a first housing 30 which is upright and substantially perpendicular to the bottom surface 24. The housing 30 has a first end 31 and a second end 33. The first end 31 of the housing 30 has an opening 32 formed therein. In its preferred embodiment, the housing 30 has a U-shaped form extending along the longitudinal axis of the first base 20.

As shown in FIGS. 1 and 2, and in detail in the cross-sectional views of FIGS. 3–6, the first section includes three upstanding first base locking members 40, 42, and 44 located within the housing 30 and supported from the base 20. While three locking members 40, 42, 44 are shown, it should be understood that a lesser or greater number of similar locking members may be used, depending upon the length of a needle supported by these members. The first base locking members 40, 42, 44 are axially aligned within the housing 30 and are disposed at predetermined spacings relative to one another. A pair of upstanding, web-like support members 50 are integrally molded to the top surface 22 of the base 20, and are substantially perpendicular to the base 20. The support members 50 are also disposed at predetermined distances relative to one another and are alternately positioned to the locking members 40, 42 and 44. The support members 50 define V-shaped notches 55 at the exposed upper end thereof Again, while two support members 50 are shown in the preferred embodiment, it also should be understood that more or less numbers of support members may be used, as desired, without departing from this invention.

With reference to the detailed view of FIG. 5, the first base locking members 42 and 44 each comprise a body 142 and a hook member 143 positioned at the distal end of the body 142. The hook portion 143 lies in a plane substantially parallel of the plane of the base 20. With reference to FIG. 6, it will be noted that the intermediate locking member 40 contains a body 140 with a hook portion 141 facing in a direction opposite to the orientation of each of the hook members 143 of the adjacent locking members 42 and 44.

Again, with reference to FIGS. 1 and 2, the second section 12 comprises a second base 60 having a top surface 62 and a flat bottom surface 64. A second housing portion 70 is integrally molded with the second section 12 (as well as with the hinge 90 and the first section 11). The housing 70 is substantially perpendicular to the top and bottom surfaces 62 and 64 of the second base 60. The housing 70 defines a first end 71 and a second end 73. The second end 73 of the housing 70 includes an opening 72 formed therein. As stated previously, the second end 73 of the housing 70 is coupled to the first end 31 of the housing 30 by means of an integrally formed hinge member 90. Also, the second base 60 includes a locking mechanism 80 arranged to connect with a cooperating locking mechanism 81, integrally molded with the bottom surface 24 of the first base 30.

The second section 12, as seen in the views FIGS. 1 and 2, contains a second base locking member 46 located within the confines of the housing 70 and extending away from the base 60. The locking member 46 is similar to the locking members 40, 42 and 44 and is formed integrally with the second section 12 and extends substantially perpendicular to the base 60.

With reference to FIG. 3, the second base locking member 46 comprises a body 146 and a hook portion 147. The hook portion 147 lies substantially perpendicular to the body 146 and substantially parallel with the plane of the base 60.

With particular reference to views of FIGS. 1, 2, 11, and 12, the present invention finds application for the protection of hypodermic needles, and particularly hypodermic needle assemblies 100 a luer 105, a first needle 101 and a second needle 102 pointed in opposite directions relative to one another. After the dentist uses a hypodermic needle assembly 100 to administer medication to a patient, he or she inserts the syringe (not shown) with the first needle 101 into the first housing 30. The assembly 100 engages with the first base locking members 40, 42, and 44. The first needle 101 will then be supported by the notches 55 of each of the support members 50 and will be further securely retained within the first housing 30 by the first base locking members 40, 42, and 44. The integrally molded construction also will provide a flexibility which will cause the needle 101 to be additionally secured relative to each of the locking members 40, 42, 44 and the support members 50. Next, the dentist disengages the luer 105 from the syringe (not shown), to thereby expose the second needle 102. Finally, the second housing 70 is pivoted about its integrally molded hinge 90. This action causes the second housing 70 to wrap around and cover the second needle 102. The second needle 102 engages the second base locking member 46 and will be securely retained within the second housing 70 and with reference to the locking mechanism supporting the remaining structure of the luer 105 and the needle 101. The locking mechanism 80 of the second base 60 will snap into place with respect to the locking mechanism 81 formed in the first section 11, and thereby couple the second section 12 with the first section 11 to safeguard the oppositely disposed first needle 101 and second needle 102.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. An anti-stick adapter for housing a needle assembly, said needle assembly having a first needle portion and a second needle portion, said anti-stick adapter comprising:

a first section comprising a first base and a first housing;

said first base, having a top surface and a bottom surface;

said first housing secured to said top surface of said first base;

said first housing having a first opening formed therein;

at least one first base locking member for retaining said first needle portion, said first base locking member secured to and supported by said top surface of said first base;

at least one support member for supporting said first needle portion, said support member secured to and supported by said top surface of said first base;

a second section comprising a second base and a second housing;

said second base, having a top surface and a bottom surface;

said second housing secured to and supported by said top surface of said second base having a second opening formed therein;

said second section flexibly connected to said first section such that said first and second openings of said first and second housings may be pivoted to face one another;

at least one second base locking member for retaining said second needle portion, said second base locking member secured to and supported by said top surface of said second base.

2. The anti-stick adapter of claim 1, wherein said at least one first base locking member is contained within said first housing, and extends within and substantially perpendicular to said top surface of said at least one first base, and wherein said first base locking member comprises an upstanding body portion and a hook portion at its distal end and arranged to retain said first needle portion.

3. The anti-stick adapter of claim 2, wherein said at least one support member is contained within said first housing, and disposed substantially perpendicular to said top surface of said first base and defining a first needle retaining notch at its distal end.

4. The anti-stick device of claim 1, wherein said device includes a latching mechanism comprising a first member and a cooperating second member for retaining said first and second housings in facing relationship after insertion of said needle assembly;

said first member integrally molded with said first section;

said second member integrally molded with said second section.

5. The anti-stick adapter of claim 1, wherein said at least one second base locking member is contained within said second housing, and extends within and substantially perpendicular to said top surface of said second base.

* * * * *